(12) United States Patent
Rogers

(10) Patent No.: US 9,907,617 B2
(45) Date of Patent: Mar. 6, 2018

(54) MEDICAL IMPLEMENT CLEANING DEVICE

(71) Applicant: 3M Innovative Properties Company, Saint Paul, MN (US)

(72) Inventor: Bobby E. Rogers, San Diego, CA (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 587 days.

(21) Appl. No.: 13/844,687

(22) Filed: Mar. 15, 2013

(65) Prior Publication Data

US 2014/0261581 A1    Sep. 18, 2014

(51) Int. Cl.

| | | |
|---|---|---|
| *A61J 1/00* | (2006.01) |
| *A61L 2/16* | (2006.01) |
| *A61L 2/18* | (2006.01) |
| *A61L 2/23* | (2006.01) |
| *A61M 39/16* | (2006.01) |
| *A61M 39/20* | (2006.01) |
| *B08B 1/00* | (2006.01) |
| *A61B 19/00* | (2006.01) |

(Continued)

(52) U.S. Cl.
CPC .............. *A61B 19/34* (2013.01); *A61B 50/30* (2016.02); *A61B 90/70* (2016.02); *A61J 1/00* (2013.01); *A61L 2/16* (2013.01); *A61L 2/186* (2013.01); *A61L 2/23* (2013.01); *A61M 39/16* (2013.01); *A61M 39/162* (2013.01); *A61M 39/20* (2013.01); *B08B 1/00* (2013.01); *A61B 2050/3008* (2016.02); *A61L 2202/24* (2013.01); *A61M 2205/11* (2013.01)

(58) Field of Classification Search
CPC ......... A61B 19/34; A61B 50/30; A61B 90/70; A61B 2050/3008; A61L 2/16; A61L 2/186; A61L 2/23; A61L 2202/24; A61M 39/16; A61M 39/162; A61M 39/20; A61M 2205/11; B08B 1/00
USPC ... 134/56 R, 147, 166 C, 166 R, 169 C, 172, 134/116, 198, 201; 422/28, 113, 292, 422/294, 300, 302
See application file for complete search history.

(56) References Cited

U.S. PATENT DOCUMENTS

| | | |
|---|---|---|
| 1,744,026 A | 1/1930 | Baltzley |
| 1,841,597 A | 1/1932 | Hammer et al. |
| 1,937,492 A | 11/1933 | Merolle |

(Continued)

FOREIGN PATENT DOCUMENTS

| | | |
|---|---|---|
| CN | 101618384 | 1/2010 |
| CN | 102170978 | 8/2011 |

(Continued)

OTHER PUBLICATIONS

U.S. Appl. No. 60/815,806, filed Jun. 22, 2006, Anderson et al.

(Continued)

*Primary Examiner* — Levon J Shahinian
(74) *Attorney, Agent, or Firm* — 3M Innovative Properties Company; Lynn R. Hunsberger

(57) ABSTRACT

A cleaning device for a medical implement is disclosed. The cleaning device includes a housing, a cleaning agent within the housing, and a movable septum in the housing that maintains the cleaning agent within the housing until receipt by the housing of the site of the medical implement. Related apparatus, systems, techniques, and articles are also described.

13 Claims, 12 Drawing Sheets

(51) Int. Cl.
*A61B 50/30* (2016.01)
*A61B 90/70* (2016.01)

(56) References Cited

U.S. PATENT DOCUMENTS

| | | |
|---|---|---|
| 2,322,701 A | 6/1943 | Nesset et al. |
| 2,341,285 A | 2/1944 | Petrullo |
| 2,731,963 A | 1/1956 | Blank |
| 2,740,480 A | 4/1956 | Cox et al. |
| 2,993,612 A | 7/1961 | Trautvetter |
| 3,120,879 A | 2/1964 | Warner |
| 3,199,748 A | 8/1965 | Bross |
| 3,362,587 A | 1/1968 | Postel et al. |
| 3,391,847 A | 7/1968 | Christine et al. |
| 3,405,831 A | 10/1968 | Hudson et al. |
| 3,431,548 A | 3/1969 | Busier et al. |
| 3,435,978 A | 4/1969 | Wittwer |
| 3,443,686 A | 5/1969 | Raymond et al. |
| 3,651,972 A | 3/1972 | Itoh |
| 3,771,685 A | 11/1973 | Micallef |
| 3,818,627 A | 6/1974 | Lebensfeld |
| 3,979,001 A | 9/1976 | Bogert |
| 3,987,921 A | 10/1976 | Aichinger |
| 3,987,930 A | 10/1976 | Fuson |
| 4,089,463 A | 5/1978 | Babiol |
| 4,169,751 A | 10/1979 | Yen |
| 4,232,677 A | 11/1980 | Leibinsohn |
| 4,257,526 A | 3/1981 | Weits et al. |
| 4,280,632 A | 7/1981 | Yuhara |
| 4,289,248 A | 9/1981 | Lynn |
| 4,335,756 A | 6/1982 | Sharp et al. |
| 4,340,148 A | 7/1982 | Beckham |
| 4,401,227 A | 8/1983 | Pehr |
| 4,432,764 A | 2/1984 | Lopez |
| 4,440,207 A | 4/1984 | Genatempo et al. |
| 4,461,394 A | 7/1984 | Sendel et al. |
| 4,530,726 A | 7/1985 | Montiel |
| 4,564,116 A | 1/1986 | Prohaska |
| 4,572,373 A | 2/1986 | Johansson |
| 4,597,758 A | 7/1986 | Aalto et al. |
| 4,624,664 A | 11/1986 | Peluso et al. |
| 4,655,762 A | 4/1987 | Rogers |
| 4,671,306 A | 6/1987 | Spector |
| 4,674,643 A | 6/1987 | Wilde et al. |
| 4,712,705 A | 12/1987 | Fuehrer |
| 4,752,983 A | 6/1988 | Grieshaber |
| 4,778,447 A | 10/1988 | Velde et al. |
| 4,798,303 A | 1/1989 | Arnold |
| 4,810,241 A | 3/1989 | Rogers |
| 4,991,629 A | 2/1991 | Ernesto et al. |
| 5,065,783 A | 11/1991 | Ogle, II |
| 5,078,693 A | 1/1992 | Shine |
| 5,143,104 A | 9/1992 | Iba et al. |
| 5,169,033 A | 12/1992 | Shay |
| 5,184,742 A | 2/1993 | DeCaprio et al. |
| 5,242,425 A | 9/1993 | White et al. |
| 5,263,606 A | 11/1993 | Dutt et al. |
| 5,277,311 A | 1/1994 | Hollister |
| 5,292,020 A | 3/1994 | Narin |
| 5,385,372 A | 1/1995 | Utterberg |
| 5,385,378 A | 1/1995 | Hakamada et al. |
| 5,398,837 A | 3/1995 | Degrassi |
| 5,409,471 A | 4/1995 | Atkinson et al. |
| 5,433,705 A | 7/1995 | Giebel |
| 5,445,270 A | 8/1995 | Dratz |
| 5,535,771 A | 7/1996 | Purdy et al. |
| 5,554,135 A | 9/1996 | Menyhay |
| 5,624,402 A | 4/1997 | Imbert |
| 5,694,978 A | 12/1997 | Heilmann et al. |
| 5,702,017 A | 12/1997 | Goncalves |
| 5,743,884 A | 4/1998 | Hasson et al. |
| 5,743,894 A | 4/1998 | Swisher |
| 5,792,120 A | 8/1998 | Menyhay |
| 5,807,345 A | 9/1998 | Grabenkort |
| 5,807,347 A | 9/1998 | Bonaldo |
| 5,947,954 A | 9/1999 | Bonaldo |
| 5,951,519 A | 9/1999 | Utterberg |
| 5,954,957 A | 9/1999 | Chin-Loy et al. |
| 5,989,227 A | 11/1999 | Vetter et al. |
| 6,004,299 A | 12/1999 | Arai et al. |
| 6,027,482 A | 2/2000 | Imbert |
| 6,036,672 A | 3/2000 | Allen et al. |
| 6,045,539 A | 4/2000 | Menyhay |
| 6,102,223 A | 8/2000 | Montgomery |
| 6,116,468 A | 9/2000 | Nilson |
| 6,190,364 B1 | 2/2001 | Imbert |
| 6,196,998 B1 | 3/2001 | Jansen et al. |
| 6,227,391 B1 | 5/2001 | King |
| 6,250,315 B1 | 6/2001 | Ernster |
| 6,293,293 B1 | 9/2001 | Wrigley et al. |
| 6,299,131 B1 | 10/2001 | Ryan |
| 6,364,862 B1 | 4/2002 | Bonilla |
| 6,394,983 B1 | 5/2002 | Mayoral et al. |
| 6,520,935 B1 | 2/2003 | Jansen et al. |
| 6,523,686 B1 | 2/2003 | Bae |
| 6,524,295 B2 | 2/2003 | Daubert et al. |
| 6,527,751 B2 | 3/2003 | Fischer et al. |
| 6,622,882 B2 | 9/2003 | Smith |
| 6,821,267 B2 | 11/2004 | Veillon, Jr. et al. |
| 6,880,801 B2 | 4/2005 | Matkovich et al. |
| 6,911,025 B2 | 6/2005 | Miyahara |
| 6,913,157 B2 | 7/2005 | Oh |
| 7,083,605 B2 | 8/2006 | Miyahara |
| 7,090,191 B2 | 8/2006 | Matkovich et al. |
| 7,118,560 B2 | 10/2006 | Bonaldo |
| 7,188,623 B2 | 3/2007 | Anderson et al. |
| 7,198,611 B2 | 4/2007 | Connell et al. |
| 7,282,186 B2 | 10/2007 | Lake, Jr. et al. |
| 7,316,669 B2 | 1/2008 | Ranalletta |
| 7,329,235 B2 | 2/2008 | Bertron et al. |
| 7,329,249 B2 | 2/2008 | Bonaldo |
| 7,427,275 B2 | 9/2008 | DeRuntz et al. |
| 7,452,349 B2 | 11/2008 | Miyahara |
| 7,500,964 B2 | 3/2009 | Shaw et al. |
| 7,530,977 B2 | 5/2009 | Lodi |
| 7,682,561 B2 | 3/2010 | Davis et al. |
| 7,704,002 B2 | 4/2010 | Fisher et al. |
| 7,780,794 B2 | 8/2010 | Rogers et al. |
| 7,857,793 B2 | 12/2010 | Raulerson et al. |
| 7,922,701 B2 | 4/2011 | Buchman |
| 7,931,618 B2 | 4/2011 | Wyrick |
| 7,931,877 B2 | 4/2011 | Steffens et al. |
| 7,967,779 B2 | 6/2011 | Bertron et al. |
| 7,985,302 B2 | 7/2011 | Rogers et al. |
| 7,988,676 B1 | 8/2011 | Gray |
| 8,061,544 B2 | 11/2011 | Frishman |
| 8,105,293 B2 | 1/2012 | Pickhard |
| 8,162,899 B2 | 4/2012 | Tennican |
| 8,167,847 B2 | 5/2012 | Anderson et al. |
| 8,172,813 B2 | 5/2012 | Janish |
| 8,177,768 B2 | 5/2012 | Leinsing |
| 8,197,749 B2 | 6/2012 | Howlett et al. |
| 8,206,514 B2 | 6/2012 | Rogers et al. |
| 8,231,587 B2 | 7/2012 | Solomon et al. |
| 8,277,422 B2 | 10/2012 | Oliver et al. |
| 8,287,491 B2 | 10/2012 | Burns et al. |
| 8,296,893 B2 | 10/2012 | Vinci et al. |
| 8,303,548 B2 | 11/2012 | Ito et al. |
| 8,641,681 B2 | 2/2014 | Solomon et al. |
| 8,647,326 B2 | 2/2014 | Solomon et al. |
| 8,832,894 B2 | 9/2014 | Rogers et al. |
| 8,834,650 B2 | 9/2014 | Rogers et al. |
| 2001/0003150 A1 | 6/2001 | Imbert |
| 2002/0133124 A1 | 9/2002 | Leinsing et al. |
| 2004/0024357 A1 | 2/2004 | Pelkey et al. |
| 2004/0030321 A1 | 2/2004 | Fangrow |
| 2004/0039341 A1 | 2/2004 | Ranalletta |
| 2004/0138626 A1 | 7/2004 | Cote et al. |
| 2004/0171993 A1 | 9/2004 | Bonaldo |
| 2004/0172006 A1 | 9/2004 | Bonaldo |
| 2004/0195136 A1 | 10/2004 | Young et al. |
| 2004/0258560 A1 | 12/2004 | Lake et al. |
| 2005/0124970 A1 | 6/2005 | Kunin et al. |
| 2005/0147524 A1 | 7/2005 | Bousquet |

(56) References Cited

U.S. PATENT DOCUMENTS

| | | |
|---|---|---|
| 2005/0147525 A1 | 7/2005 | Bousquet |
| 2005/0214185 A1 | 9/2005 | Castaneda |
| 2006/0030827 A1 | 2/2006 | Raulerson et al. |
| 2006/0048313 A1 | 3/2006 | Yamaki |
| 2006/0189961 A1 | 8/2006 | Miyahara |
| 2006/0253103 A1 | 11/2006 | Utterberg et al. |
| 2007/0106205 A1 | 5/2007 | Connell et al. |
| 2007/0106229 A1 | 5/2007 | Wong |
| 2007/0112333 A1 | 5/2007 | Hoang et al. |
| 2007/0156118 A1 | 7/2007 | Ramsey et al. |
| 2007/0176117 A1 | 8/2007 | Redmond et al. |
| 2008/0019889 A1 | 1/2008 | Rogers et al. |
| 2008/0027399 A1 | 1/2008 | Harding et al. |
| 2008/0038167 A1 | 2/2008 | Lynn |
| 2008/0039803 A1 | 2/2008 | Lynn |
| 2008/0086091 A1 | 4/2008 | Anderson et al. |
| 2008/0095680 A1 | 4/2008 | Steffens et al. |
| 2008/0128646 A1 | 6/2008 | Clawson |
| 2008/0132880 A1 | 6/2008 | Buchman |
| 2008/0147047 A1 | 6/2008 | Davis et al. |
| 2008/0172007 A1* | 7/2008 | Bousquet ............. A61M 39/20 604/256 |
| 2008/0177250 A1 | 7/2008 | Howlett et al. |
| 2009/0005759 A1 | 1/2009 | Chelak |
| 2009/0008393 A1 | 1/2009 | Howlett et al. |
| 2009/0028750 A1 | 1/2009 | Ryan |
| 2009/0062766 A1 | 3/2009 | Howlett et al. |
| 2009/0099529 A1 | 4/2009 | Anderson et al. |
| 2009/0137969 A1 | 5/2009 | Colantonio et al. |
| 2009/0149819 A1 | 6/2009 | Chelak |
| 2009/0163876 A1 | 6/2009 | Chebator et al. |
| 2009/0205151 A1 | 8/2009 | Fisher et al. |
| 2010/0000040 A1 | 1/2010 | Shaw |
| 2010/0047123 A1 | 2/2010 | Solomon et al. |
| 2010/0049170 A1 | 2/2010 | Solomon et al. |
| 2010/0050351 A1 | 3/2010 | Colantonio et al. |
| 2010/0172794 A1 | 7/2010 | Ferlic et al. |
| 2010/0174162 A1 | 7/2010 | Gough et al. |
| 2010/0199448 A1 | 8/2010 | Vazales et al. |
| 2010/0312197 A1 | 12/2010 | Sano et al. |
| 2010/0313366 A1 | 12/2010 | Rogers et al. |
| 2011/0213341 A1 | 9/2011 | Solomon et al. |
| 2011/0265825 A1 | 11/2011 | Rogers et al. |
| 2011/0277788 A1 | 11/2011 | Rogers et al. |
| 2012/0022469 A1* | 1/2012 | Alpert .................. A61M 39/16 604/265 |
| 2012/0039764 A1 | 2/2012 | Solomon et al. |
| 2013/0019421 A1 | 1/2013 | Rogers et al. |
| 2013/0237911 A1 | 9/2013 | Von Schuckmann |
| 2014/0101876 A1 | 4/2014 | Rogers et al. |
| 2014/0228773 A1 | 8/2014 | Burkholz |

FOREIGN PATENT DOCUMENTS

| | | |
|---|---|---|
| DE | 2164821 A1 | 8/1972 |
| EP | 0462355 A1 | 12/1991 |
| EP | 1061000 A2 | 12/2000 |
| EP | 1977714 A1 | 10/2008 |
| EP | 2135626 A1 | 12/2009 |
| JP | 07-047137 | 2/1995 |
| JP | 07-043674 | 9/1995 |
| JP | 09-206370 A | 8/1997 |
| JP | 09-012829 U | 9/1997 |
| JP | 2001-527441 A | 12/2001 |
| JP | 2002-291906 A | 10/2002 |
| JP | 4234777 B1 | 3/2009 |
| JP | 2010-005030 | 1/2010 |
| JP | 2011-526810 | 10/2011 |
| WO | WO-94/11474 A1 | 5/1994 |
| WO | WO-98/48872 A1 | 11/1998 |
| WO | WO-00/24442 A1 | 5/2000 |
| WO | WO-2007/103998 A2 | 9/2007 |
| WO | WO-2007137056 A2 | 11/2007 |
| WO | WO-2008/100950 A2 | 8/2008 |
| WO | WO-2009136957 A1 | 11/2009 |
| WO | WO-2009/153224 A1 | 12/2009 |
| WO | WO 2010-002757 | 1/2010 |
| WO | WO 2010/039171 | 4/2010 |
| WO | WO-2011056221 A1 | 5/2011 |
| WO | WO-2011120017 A1 | 9/2011 |
| WO | WO 2011/163124 | 12/2011 |

OTHER PUBLICATIONS

U.S. Appl. No. 60/832,437, filed Jul. 21, 2006, Rogers.

Byington "Spontaneously Generating Life in Your Classroom? Pasteur, Spallanzani & Science Process," *THE AMERICAN BIOLOGY TEACHER*, vol. 63, No. 5 (May 2001). pp. 340-345. Published by University of California Press on behalf of National Association of Biology Teachers.

European Patent Office, European Search Report and Opinion for EP Application No. EP 10 78 3956, date of completion of the search Mar. 12, 2014, 7 pgs.

European Patent Office, Supplementary Partial European Search Report and Opinion for EP Application No. 07 75 8117 date of completion of the search Nov. 22, 2012, 6 pgs.

International Search Report and Written Opinion issued in International Application No. PCT/US2008/053744, dated Jul. 22, 2009.

International Search Report and Written Opinion issued in International Application No. PCT/US2012/025517, dated Nov. 9, 2012.

International Search Report and Written Opinion issued in International Application No. PCT/US2013/044167, dated Oct. 16, 2013.

International Standard ISO 594-2. "Conical Fitting with 6% (Luer) Taper for Syringes, Needles and Certain Other Medical Equipment—Part 2: Lock Fittings". Reference No. ISO 594-2:1998(E). Second edition. (Sep. 1, 1998)1:11.

Japanese Patent Office, Japanese Notice of Reasons for Rejection for Japanese Patent Application No. 2008-558527 dated Apr. 12, 2012.

Japanese Patent Office, Japanese Notice of Reasons for Rejection for Japanese Patent Application No. 2008-558527 dated Apr. 2, 2013.

Material Properties of Polyamide (Nylon), www.madeitfrom.com, pp. 1-2. Retrieved Sep. 23, 2012.

Material Properties of Polycarbonate, www.madeitfrom.com, pp. 1-3. Retrieved Sep. 23, 2012.

Material Properties of Polypropylene, www.madeitfrom.com, pp. 1-2. Retrieved Sep. 23, 2012.

Menyhay et al. "Disinfection of Needleless Catheter Connectors and Access Ports with Alcohol May Not Prevent Microbial Entry: The Promise of a Novel Antiseptic-Barrier Cap". *The University of Chicago Press on behalf of The Society for Healthcare Epidemiology of America. Infect Control Hosp Epidemiol* vol. 27(2006):23-27.

Menyhay Healthcare Systems LLC available at http://www.menyhaymedical.comimenyhay.html (retrieved Nov. 8, 2013).

The International Bureau of WIPO, PCT International Preliminary Report on Patentability and Written Opinion of the International Searching Authority for International Application No. PCT/US2007/063534 dated Nov. 21, 2007.

Value Plastics Inc, Luer Connectors, http://www.valueplasctics.com/search/search.aspx, pp. 1-2. Retrieved Sep. 23, 2012.

International Search Report and Written Opinion issued in International Application No. PCT/US2014/026716, dated Jun. 12, 2014.

* cited by examiner

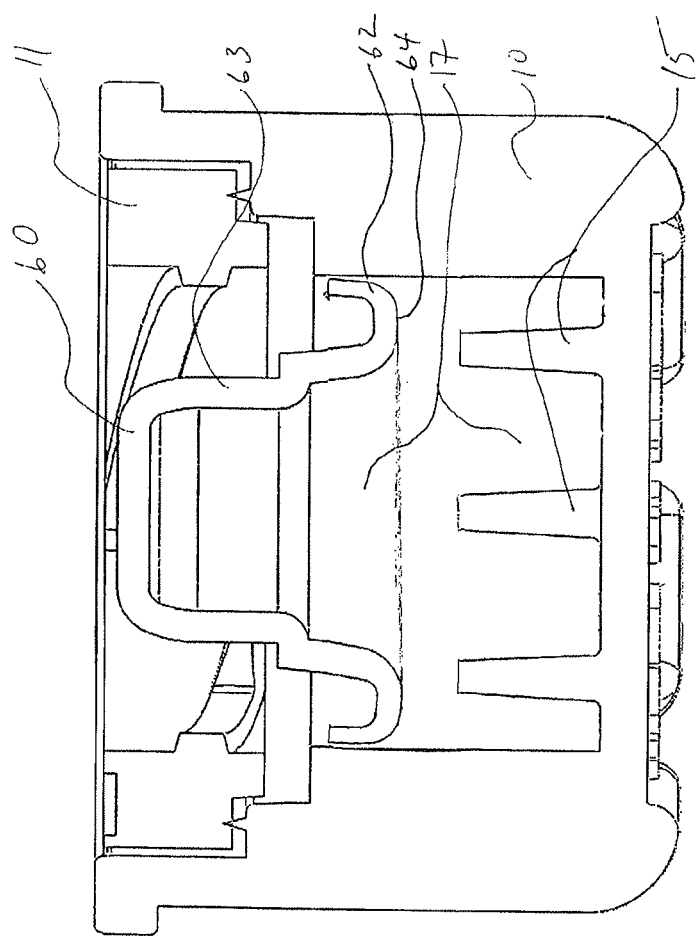

ns and inadequate training, swabbing is often overlooked or is poorly executed. A poorly swabbed site can carry microorganisms that, if allowed to enter a patient's body, can cause serious infection. In addition, supervisory oversight is nearly impossible, because unless a supervisor can actually observe the swabbing being performed, the supervisor cannot know whether or not it was done properly or performed at all. Further, without at least a sufficient microscopic examination for microbial residue, there may be no evidence of an alcohol swab being performed. Thus, a need exists for an apparatus and technique for cleaning a site on a medical implement prior to contact with a patient, and which will eliminate technique-related issues and training issues, and provide an unequivocal indicator that a site is clean prior to accessing a patient's vascular system.

MEDICAL IMPLEMENT CLEANING DEVICE

TECHNICAL FIELD

The subject matter described herein relates to a cleaning device for medical implements.

BACKGROUND

Within the medical field, and in particular the area of infusion of fluids or aspiration of fluids to or from a patient, there is a need to prevent the transmission of pathogens into or onto a patient from a potentially contaminated surface of a medical implement, or "site". Such pathogens include microorganisms such as bacteria and viruses. The transmission of pathogens into a patient may result in an infection that could be life threatening. Specific to healthcare settings, the term "nosocomial infection" describes those infections that originate from or occur in a hospital or hospital-like setting. In the U.S., nosocomial infections are estimated to occur in at least 5% of all acute care hospitalizations. The estimated incidence is more than two million cases per year, resulting in an added expenditure in excess of $4.5 billion. Nosocomial infections are estimated to more than double the mortality and morbidity risks of any admitted patient, and likely result in about 90,000 deaths a year in the United States. Common sites for such transmissions are found on such medical implements as a luer port, vial, needle free valve, or an injection port of a vessel, tubing, or catheter. Even non-intrusive medical implements such as stethoscopes can transmit pathogens to a patient. The incidence of infection in patients is presently numerous and increasing, and Infection Control Practitioners (ICP's) often cite improper cleaning of sites as a major source of these infections.

Traditionally, cleaning a potentially contaminated surface includes a protocol of alcohol swabbing prior to making the necessary connections to the site. Today alcohol swabs, a small pad of cotton gauze soaked in isopropyl alcohol, are packed individually in a foil package. The foil package is relatively inexpensive, and is used to retain the alcohol within the package and to prevent evaporation. Properly used, the package is opened at or near the site to be swabbed. With gloved hands, the pad is removed by a healthcare provider and wiped across the top and side surfaces of the site, and the pad and foil package are discarded. The site should be allowed to dry, usually twenty to thirty seconds, immediately prior to making any connection. This "drying" period is important: when alcohol dries, it breaks open the cellular walls of microorganisms, thereby killing them.

Unfortunately, because of increased duties and responsibilities, shrinking nursing staffs, and inadequate training, swabbing is often overlooked or is poorly executed. A poorly swabbed site can carry microorganisms that, if allowed to enter a patient's body, can cause serious infection. In addition, supervisory oversight is nearly impossible, because unless a supervisor can actually observe the swabbing being performed, the supervisor cannot know whether or not it was done properly or performed at all. Further, without at least a sufficient microscopic examination for microbial residue, there may be no evidence of an alcohol swab being performed. Thus, a need exists for an apparatus and technique for cleaning a site on a medical implement prior to contact with a patient, and which will eliminate technique-related issues and training issues, and provide an unequivocal indicator that a site is clean prior to accessing a patient's vascular system.

SUMMARY

A cleaning device, system, and method of operating the same in a medical environment are disclosed. The cleaning device includes a housing, a cleaning agent within the housing, and a movable septum in the housing that maintains the cleaning agent within the housing until receipt by the housing of the site of the medical implement.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated herein and constitute a part of this specification, show certain aspects of the subject matter disclosed herein and, together with the description, help explain some of the principles associated with the subject matter disclosed herein. In the drawings.

FIG. 11 is a cross sectional view of a movable septum;

Like reference symbols in the various drawings indicate like elements.

DETAILED DESCRIPTION

In accordance with preferred implementations, a cleaning device can include a cap and a movable septum disposed within the cap. The movable septum can contain a cavity that holds a cleaning agent. When a medical implement is inserted into the cleaning device, the cleaning agent can flow around the septum and be applied to the medical implement. This configuration obviates the need for a foam or wet pad/compressible material that are common in conventional medical implement cleaning devices.

The cleaning agent can be any chemical, substance or material that cleans the site of bacterial or viral microorganisms, or any carrier that contains such chemical, substance or material. Examples of a cleaning agent include, but are not limited to, isopropyl alcohol, chlorhexidine, povidone-iodine, hydrogen peroxide, soap, and hydrochloric acid. In some implementations, the cleaning agent is a fluid or liquid, and can also be implemented as a thixotropic gel, a powder, or other state.

The term "medical implement" can denote any tool or object that can be used in a medical setting and that connects to a site cleaning device as described herein. Examples of medical implements include, but are not limited to, access ports on tubing sets (extension sets, T-connectors and IV sets), access ports on catheters (both peripheral and central lines), needle free valves, stopcocks, luer connectors, stethoscopes and other components or devices whereby regular cleaning is desired. Medical implements are commercially available in standard sizes. Thus, the end or opening of a site cleaning device can be provided with fittings to accommodate such standard size medical implements.

Figure 1:
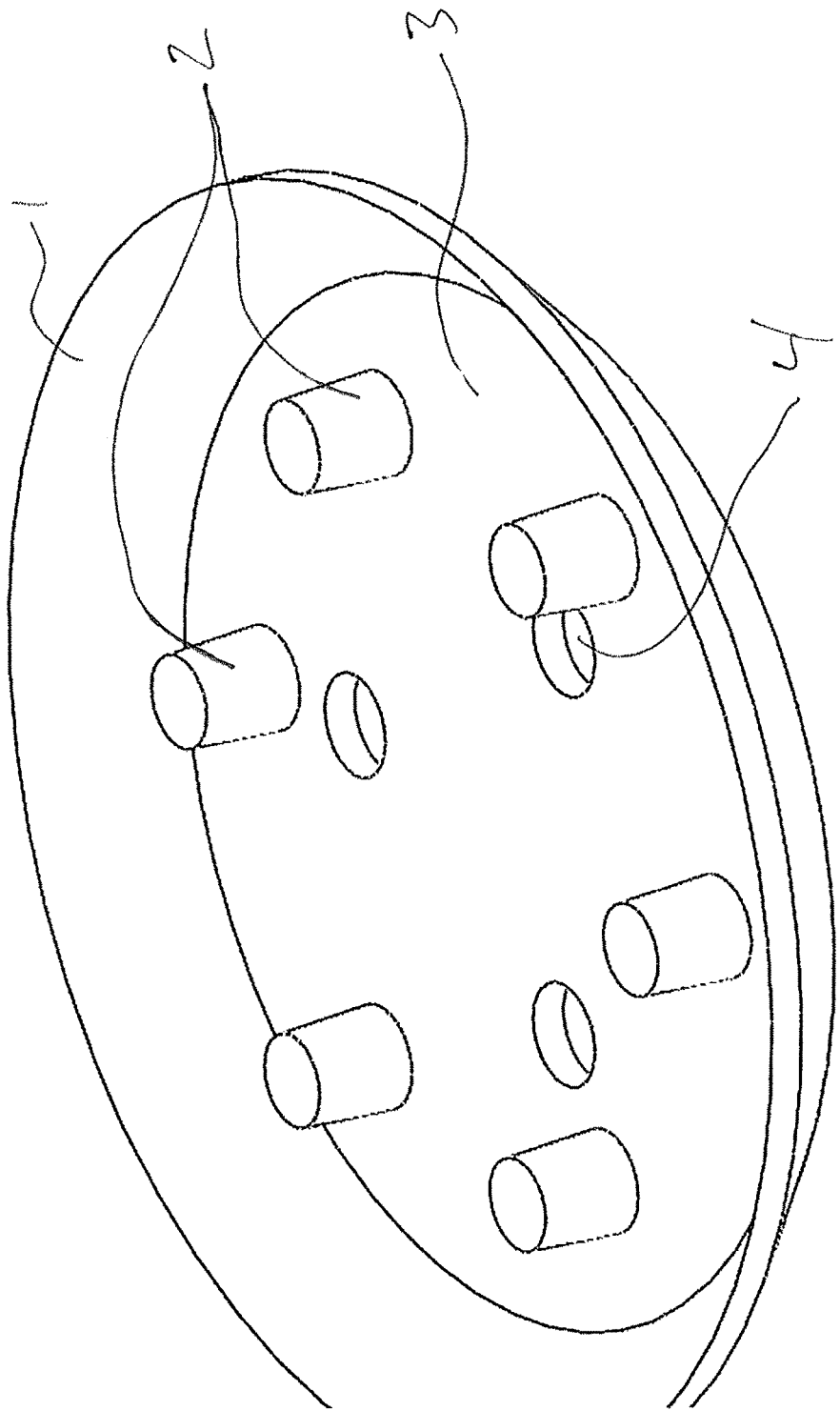
FIG. 1 illustrates a movable septum in a cleaning device.

FIG. 1 illustrates a movable septum 3 that contains a cavity. The cavity can hold a cleaning agent. Movable septum 3 can be made of high density polyethylene (HDPE) or any other plastic that is suitable for long term storage with a cleaning agent. At least one flange 1 can be disposed on the outer edges of movable septum 3. In an example, the flange 1 is a flexible outer perimeter of a circular septum 3. The flange 1 can be curved or angled up or down relative to a top surface and/or bottom surface of the septum 3. When movable septum 3 is moved into a housing, the flange 1 can flex to allow incompressible fluid stored underneath the septum 3 to flow into a region above the septum 3.

Movable septum 3 can have one or more holes 4, apertures, passageways, or fluid-permeable film or other material, that can facilitate the movement of the cleaning agent from one side to another, particularly when the cleaning agent is under pressure, i.e. by the septum 3 being pushed into the housing by a site of a medical implement. In some implementations, movable septum 3 can have no holes at all. The holes 4 can have dimensions that allow the surface tension of the cleaning agent to stay below movable septum 3, particularly in a non-pressurized or low-pressure state. In some implementations, the cleaning agent can be selected such that its viscosity is high enough to keep the cleaning agent in place below movable septum 3. The holes 4 can be sized or configured to release pressure in the cleaning agent at a particular pressure threshold.

Although movable septum 3 is illustrated as having a substantially round and flat shape, any shape can be used. In preferred implementations, the septum 3 has a shape, including a peripheral edge, that corresponds to an internal dimension of the housing. The top surface of movable septum 3 can include one or more raised structures 2, which can be frustoconical, conical, squared or any other shape. Raised structures 2 can maintain a space between a surface of the medical implement and the top surface of the movable septum 3. In some implementations, raised structures 2 can have a depressed (rather than raised) shape, which allow mating of some or a portion of the top surface of the movable septum 3 with the surface of the medical implement that is inserted into the housing, or over which the housing is placed or positioned.

Figure 2:
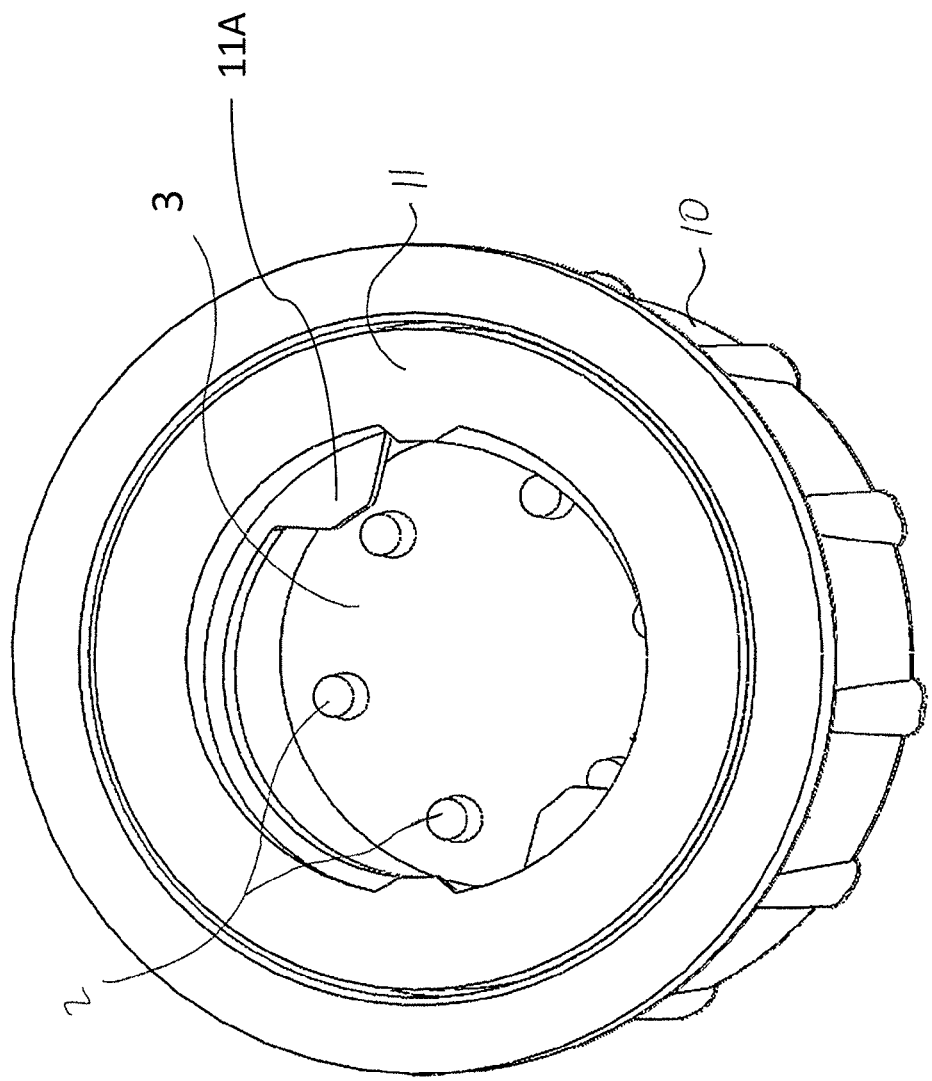
FIG. 2 is a top view of a housing having a movable septum.

FIG. 2 is a top view of a housing 10 that contains a movable septum 3. The housing includes at least one opening for receiving a site of a medical implement. The housing 10 can include one or more other apertures to allow venting of a cleaning solution or cleaning agent contained within the housing prior to receipt of the site of the medical implement. The one or more other aperture may be separate from the opening, or may be formed after the site of the medical implement is received within the opening of the housing.

When a site of a medical implement is inserted into housing 10, coupling mechanism 11 can fasten the medical implement to the housing. Coupling mechanism 11 can be a threaded ring. The threaded ring can be a separate component that connected with an internal surface of the housing at an opening to the housing, or which is integral to the internal face of housing 10. In some implementations, coupling mechanism 11 can be a flexible membrane, a crushed rib, a compressible material, and the like. Tabs 11A can be disposed along coupling mechanism 11 and can flex when a medical implement is inserted into housing 10. The flexing of tabs 11A can hold the medical implement in place within housing 10.

In some implementations, the coupling mechanism 11 can be configured to provide at least one of the one or more other apertures to allow venting, as described above. For example, the threads of a threaded coupling mechanism 11 can be formed to include a predetermined space between non-circumferential thread portions. Or, the coupling mechanism 11 can include any number of pathways, channels, or other openings to provide the one or more other apertures to allow venting.

Figure 3:
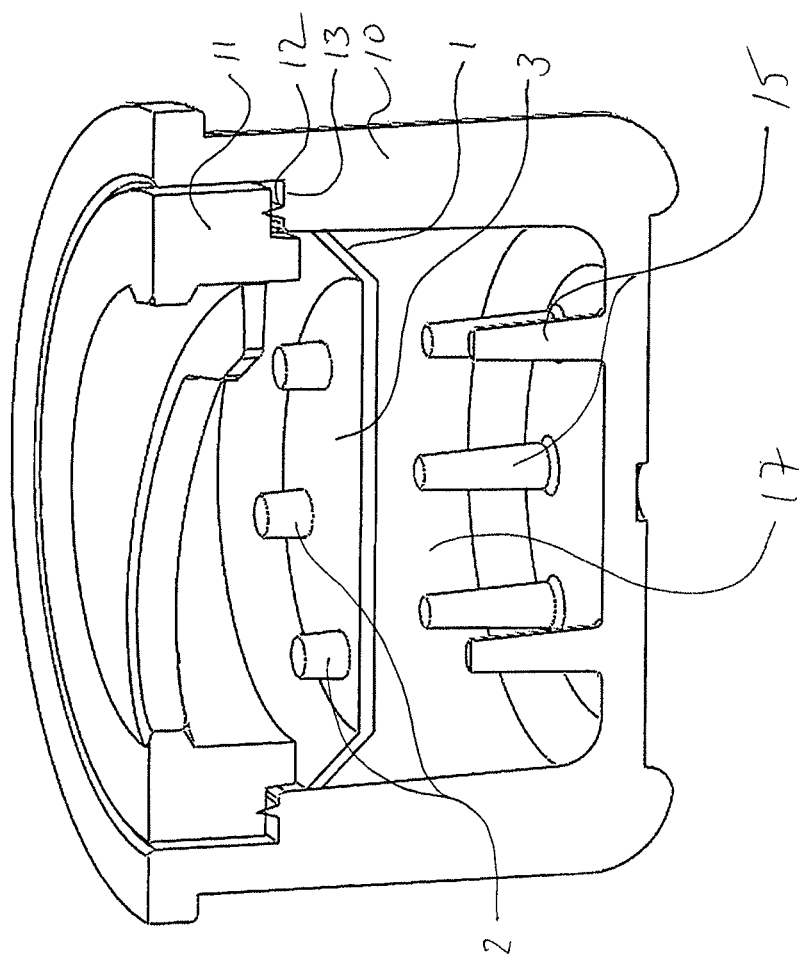
FIG. 3 is a cross sectional view of a housing and movable septum.

FIG. 3 is a cross sectional view of housing 10 and movable septum 3. Flanges 1 can press against an inner wall of housing 10 to create an interference fit. This fit can hold movable septum 3 in place within housing 10. A cleaning agent can be placed or inserted within cavity 17 below movable septum 3. The cleaning agent or solution can be put into the housing first, and then the septum 3 can be placed within the housing 10 to effectively seal or maintain the cleaning agent or solution within the housing 10 until receipt of a site of medical implement. In implementations where coupling mechanism 11 is not integral with housing 10, a mating mechanism 12 can fasten coupling mechanism 11 to the housing. The mating mechanism can be a protrusion that is heat welded to the coupling mechanism. The mating mechanism 12 can reside on or near a mating surface 13 of the housing 10.

Figure 4:
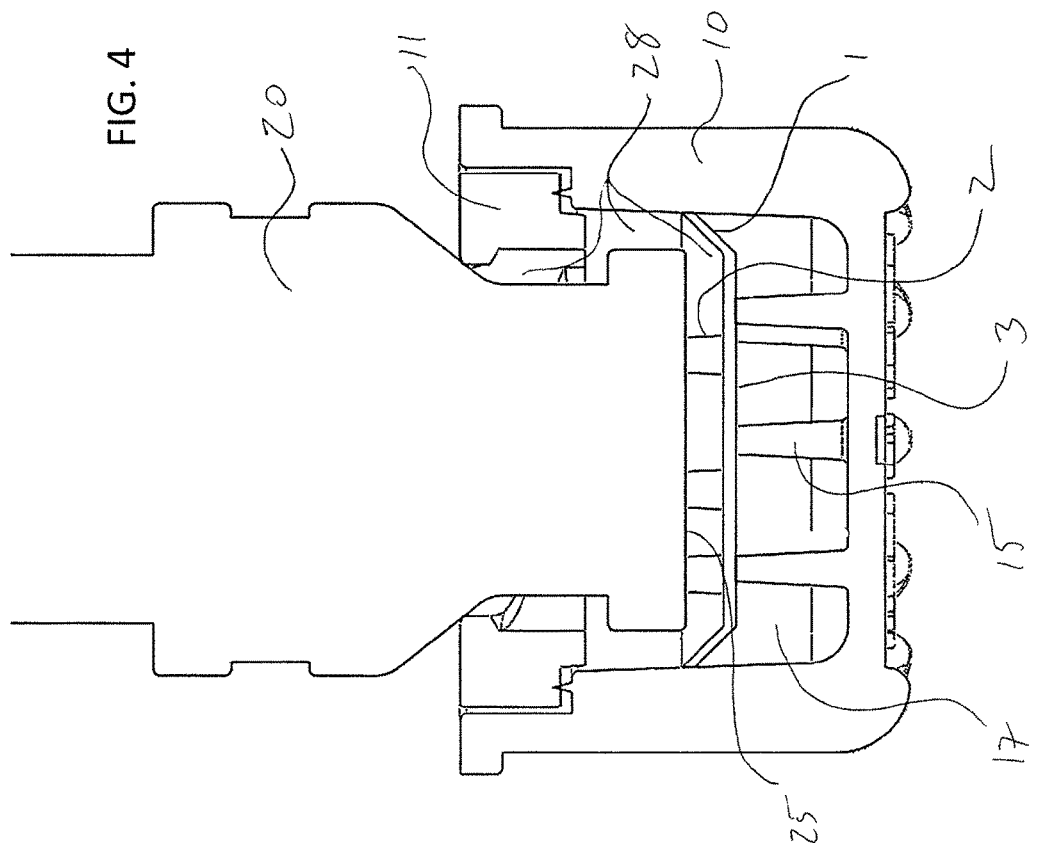
FIG. 4 illustrates a site of a medical implement inserted in a housing.

FIG. 4 illustrates a medical implement 20 inserted into housing 10. As medical implement 20 is pushed into housing 10, surface 25 on the medical implement can come into contact with frustoconical structures 2. Because frustoconical structures 2 are disposed on movable septum 3, pushing on these raised structures can cause the movable septum to move down into housing 10. As movable septum 3 moves down, the cleaning agent in cavity 17 can be forced around flanges 1 to fill space 28 above the movable septum and around sides or other surfaces of a site of a medical implement. The movable septum 3 can be stopped at a particular level within the housing by one or more protrusions 15 extending up from a distal inner surface of the housing 10 opposite the opening of the housing.

Figure 5:
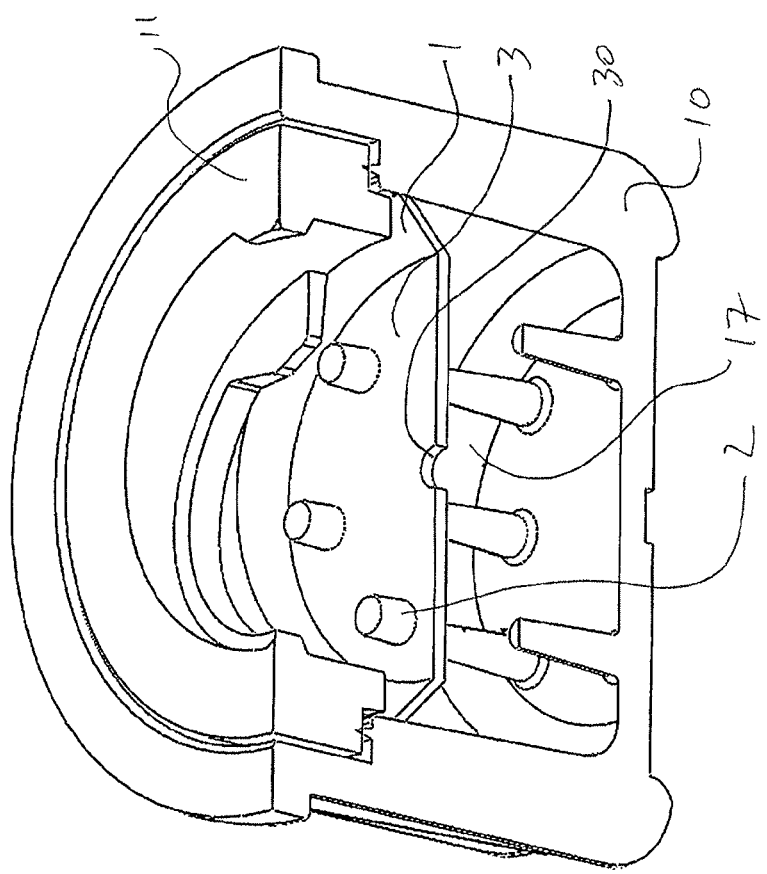
FIG. 5 is a cross sectional view of a housing with a movable septum having a single hole.
Figure 6:
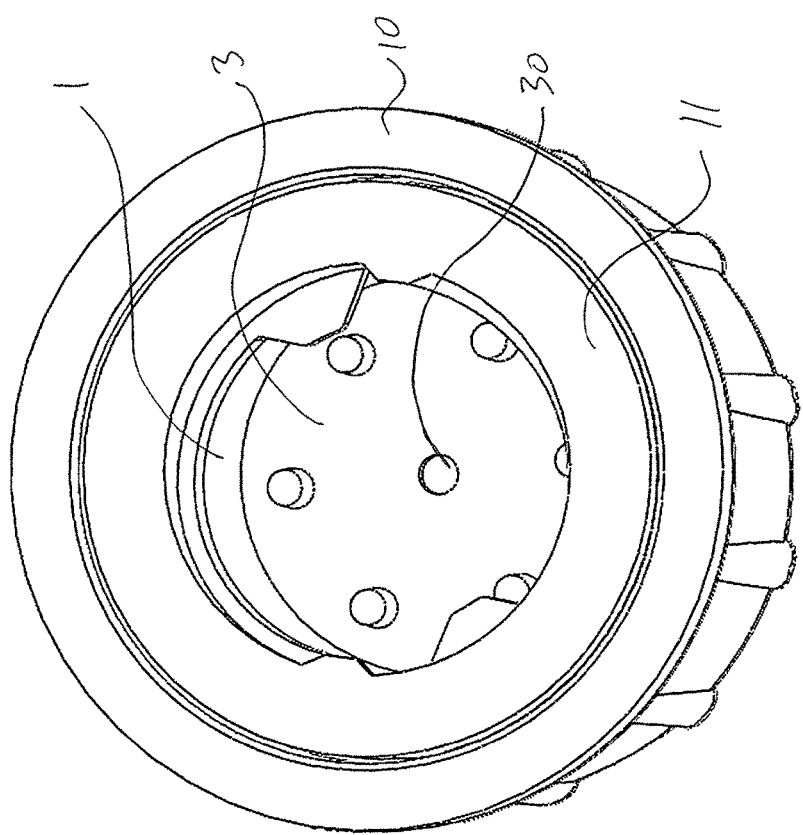
FIG. 6 is a top view of movable septum having a single hole.
Figure 7:
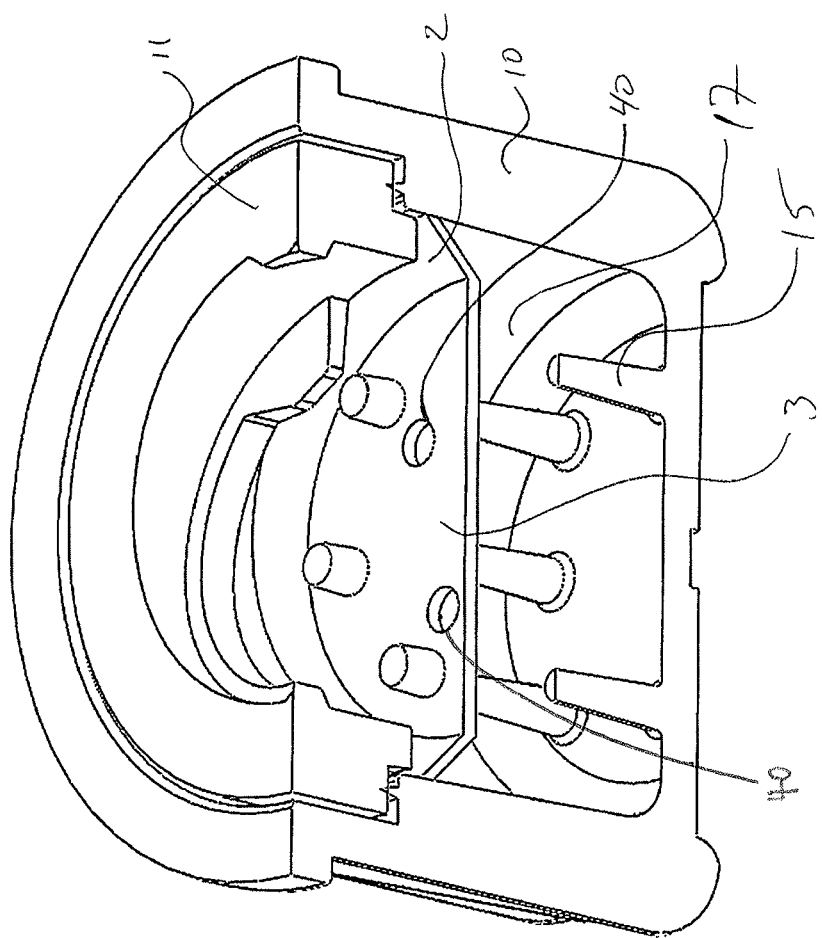
FIG. 7 is a cross sectional view of a movable septum have multiple holes.
Figure 8:
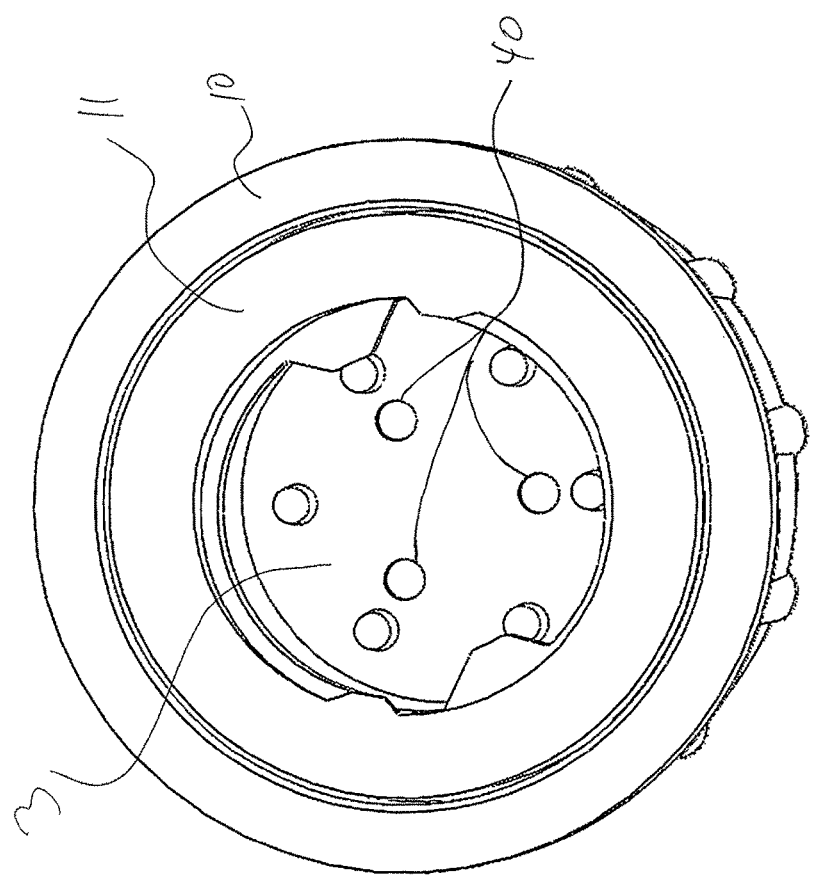
FIG. 8 is a top view of a movable septum having multiple holes.

FIGS. 5 and 7 illustrate cross sectional views of a housing 10 and a movable septum 3. In the implementation of FIG. 5, movable septum 3 has a single hole 30. In the implementation of FIG. 7, movable septum 3 has multiple holes 40. Cleaning agent in cavity 17 can flow through holes 30 and 40 into space 28 above movable septum 3 as the septum is pushed down into housing 10. In some alternative implementations, the holes 40 can be included in a mesh or fabric that is breathable, but which can maintain a fluid or solution up to a certain threshold of pressure. In a particular implementation, the septum 3 includes a peripheral ring that extends in a flexible flange, and an inner surface within the peripheral ring is such a mesh or fabric. The fabric can be made of a fabric of rigid material, such as nylon, plastic, carbon fiber, stainless steel, or the like. FIGS. 6 and 8 illustrate top views of FIGS. 5 and 7, respectively.

Figure 9:
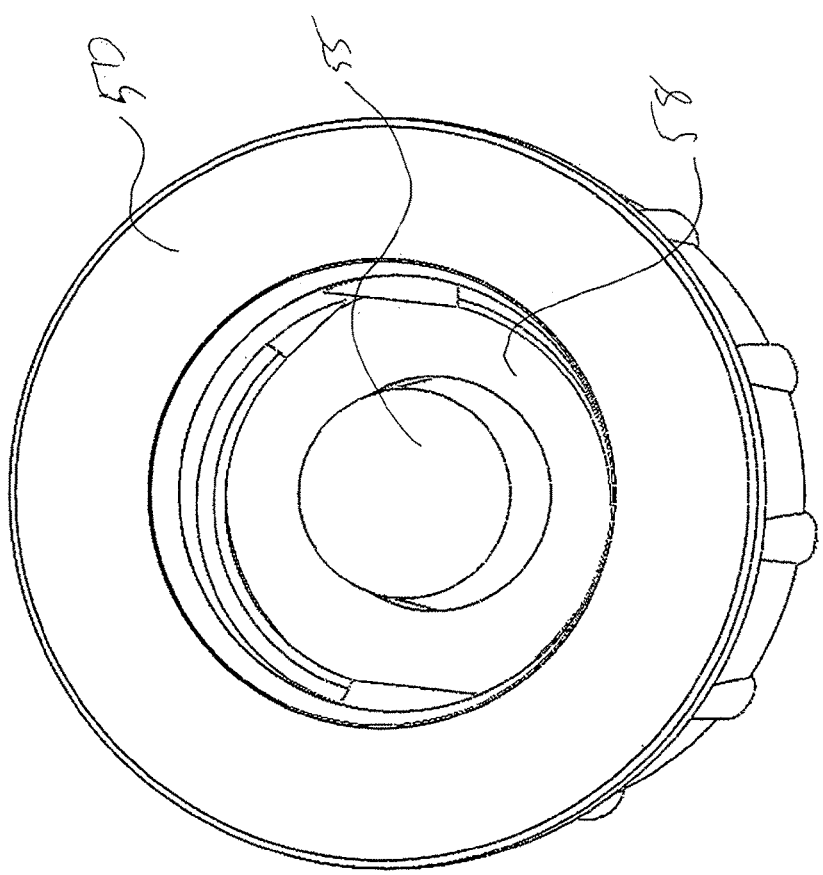
FIG. 9 is a top view of a housing with a male leur member.

FIG. 9 is a top view of a housing 50 that includes a male luer 55. A movable septum 58 is disposed around the male luer, and can move relative to the male luer 55. The male leur 55 preferably is unitary with the housing 50, and extending up from an inner surface of the housing opposite of, and toward, the opening of the housing 50. Movable septum 58 can have a doughnut shape, and male luer 55 can be positioned through the opening of the movable septum 55. When a medical implement with a female lumen or channel is inserted into housing 50, male luer 55 can mate with, and friction fit and seal, the female luer lumen or channel. Similar to movable septum 3, movable septum 58 can have a flange disposed around the outer edge of the movable septum and zero, one, or more holes disposed on the surface of the movable septum. In some implementations, movable septum 58 can have a flat surface, a raised surface with frustoconical structures, or a depressed surface. In other implementations, the movable septum 58 can have a flexible flange positioned on an inner periphery or edge of the doughnut shape, or both on inner and outer edges. Alternatively, less than a full perimeter of either inner and/or outer periphery of the movable septum may be flexible to allow passage of a cleaning agent or fluid.

Figure 10:
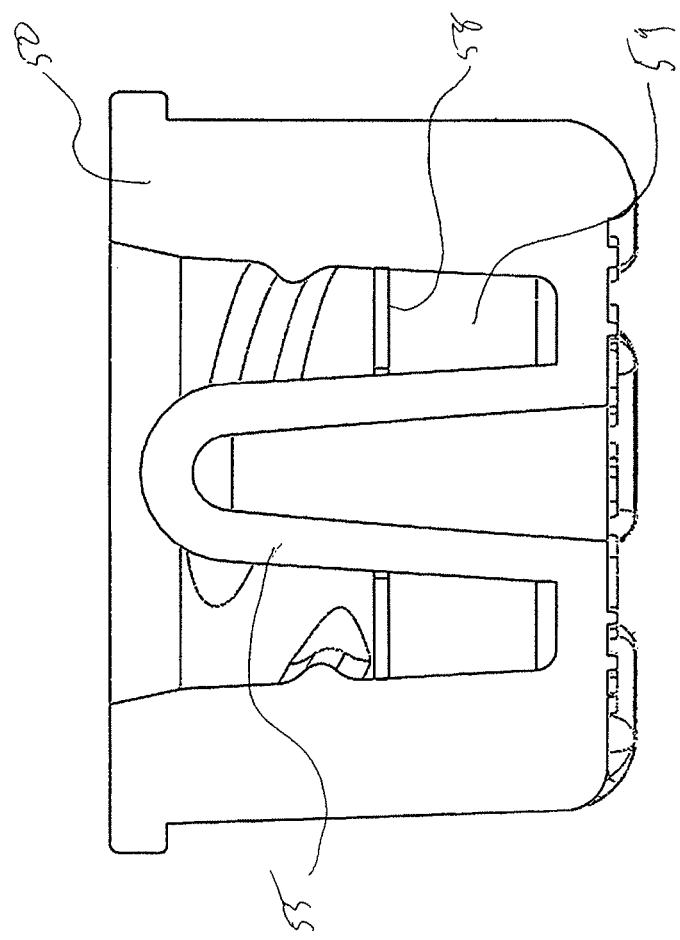
FIG. 10 is a cross sectional view of a housing of a cleaning device.

FIG. 10 is a cross sectional view of housing 50 illustrated in FIG. 9. A cleaning agent can be held in cavity 59. The housing 50 can be configured with a coupling mechanism such as a thread, a full threading, one or more flanges, protrusions, flexible tabs, an adhesive, a flexible lip or inwardly directed protrusion, or other type of coupling mechanism, or any combination thereof.

FIG. 11 is a cross sectional view of a movable septum 60 having a bottom edge 64. Movable septum 60 can act as male luer as well as a containment mechanism for a cleaning agent. Flanges 62 can press against the inner wall of housing 10 to keep the cleaning agent in cavity 17. Tapered walls 63 on movable septum 60 can be made from a substantially flexible material that allows the tapered walls to conform to an inserted female luer and seal off the inner lumen of the female luer. As described above, the housing 10 can have one or more protrusions 15 extending up from an inner surface of the housing 10 to provide a stop or limit to the movement of the movable septum 60.

Figure 12A:
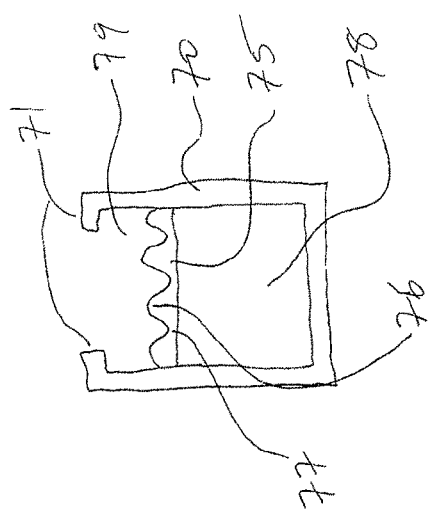
FIG. 12A is a cross sectional view of a flexible housing.

FIG. 12A is a cross sectional view of a flexible housing 70. Housing 70 can include an inwardly projecting feature 71 that can latch onto an inserted medical implement. Using inwardly projecting feature 71 can obviate the need for a separate coupling mechanism (such as a threaded ring) as described above with respect to the implementation of FIG. 2. When a medical implement is inserted into housing 70, raised elements 76 and depressed areas 77 can create a space between the medical implement and movable septum 75. Cleaning agent can reside in cavity 78 and spill into area 79 when the medical implement is inserted into housing 70.

Figure 12B:
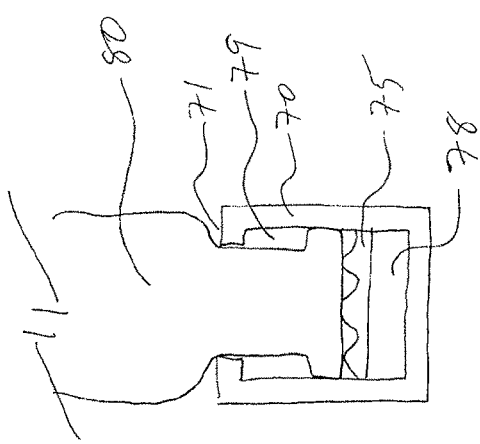
FIG. 12B is a cross sectional view of a site of a medical implement inserted into the housing of FIG. 12A.

FIG. 12B is a cross sectional view of a medical implement 80 inserted into housing 70. The insertion of medical implement 80 can push movable septum 75 down into housing 70 which, in turn can cause the chemical agent in cavity 78 to spill out into area 79.

The cleaning device described herein can include a removable seal that is disposed on an outer surface of the opening of the housing. The removable seal can be heat-welded or thermally bonded, adhered, glued, or otherwise attached to the housing and removed when the housing is to be provided on the site of the medical implement.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. Other implementations may be within the scope of the following claims.

What is claimed is:

1. A cleaning device comprising:
   a housing;
   a coupling mechanism on an inner surface of the housing;
   a cleaning agent within the housing;
   a movable septum in the housing, the movable septum including an opening that extends therethrough and a flexible flange; and
   a male luer that is unitary with the housing and extends upward from a distal inner surface of the housing opposite an opening of the housing, the male luer extending through the opening in the movable septum.

2. The cleaning device in accordance with claim 1, further comprising a removable seal coupled with the housing.

3. The cleaning device in accordance with claim 1, wherein the flexible flange is disposed along an outer edge of the movable septum and configured to create an interference fit between the movable septum and the housing.

4. The cleaning device in accordance with claim 1, further comprising one or more raised structures disposed along a top surface of the movable septum that maintain a space between a surface of a medical implement and the top surface of the movable septum.

5. The cleaning device in accordance with claim 4, wherein the one or more raised structures are frustoconical structures.

6. The cleaning device in accordance with claim 1, further comprising one or more protrusions extending upward from a distal inner surface of the housing opposite an opening of the housing, the one or more protrusions configured to stop the movable septum when the movable septum is pushed into the housing.

7. The cleaning device in accordance with claim 1, wherein the movable septum includes a flexible flange disposed along an inner edge of the opening of the movable septum.

8. The cleaning device in accordance with claim 7, wherein the movable septum further comprises a flexible flange disposed along an outer edge of the movable septum.

9. The cleaning device of claim 1, further comprising one or more holes disposed in the movable septum that allow passage of the cleaning agent from the housing to a site of a medical implement through the one or more holes when the movable septum is pushed into the housing by the medical implement.

10. The cleaning device in accordance with claim 9 wherein the one or more holes are dimensioned to prevent the passage of the cleaning agent through the one or more holes when the cleaning agent is in a low pressure state.

11. The cleaning device of claim 1, wherein the coupling mechanism is integral with the housing.

12. The cleaning device of claim 1, wherein the coupling mechanism is a threaded ring.

13. The cleaning device of claim 1, wherein the coupling mechanism is at least one of a flexible membrane, a crushed rib, and a compressible material.

* * * * *

UNITED STATES PATENT AND TRADEMARK OFFICE
CERTIFICATE OF CORRECTION

PATENT NO. : 9,907,617 B2
APPLICATION NO. : 13/844687
DATED : March 6, 2018
INVENTOR(S) : Bobby E. Rogers Page 1 of 1

It is certified that error appears in the above-identified patent and that said Letters Patent is hereby corrected as shown below:

In the Specification

<u>Column 2</u>
Line 42      Delete "leur" and insert -- luer --, therefor.

<u>Column 5</u>
Line 6       Delete "leur" and insert -- luer --, therefor.

Signed and Sealed this
Twenty-second Day of May, 2018

Andrei Iancu
*Director of the United States Patent and Trademark Office*